(12) United States Patent
Shiuey

(10) Patent No.: US 11,185,609 B2
(45) Date of Patent: Nov. 30, 2021

(54) CELL GROWTH INHIBITING COPOLYMER FOR USE IN OPHTHALMIC IMPLANTS

(71) Applicant: Yichieh Shiuey, San Jose, CA (US)

(72) Inventor: Yichieh Shiuey, San Jose, CA (US)

(73) Assignee: Keramed, Inc., Santa Ana, CA (US)

( * ) Notice: Subject to any disclaimer, the term of this patent is extended or adjusted under 35 U.S.C. 154(b) by 0 days.

(21) Appl. No.: 16/007,802

(22) Filed: Jun. 13, 2018

(65) Prior Publication Data

US 2018/0361018 A1    Dec. 20, 2018

Related U.S. Application Data

(60) Provisional application No. 62/624,284, filed on Jan. 31, 2018, provisional application No. 62/520,599, filed on Jun. 16, 2017.

(51) Int. Cl.
| | |
|---|---|
| *A61L 27/16* | (2006.01) |
| *A61L 27/18* | (2006.01) |
| *A61L 27/22* | (2006.01) |
| *C08K 5/19* | (2006.01) |
| *C08L 39/04* | (2006.01) |
| *C08L 25/06* | (2006.01) |
| *C08L 31/00* | (2006.01) |
| *C08L 33/08* | (2006.01) |
| *C08F 220/34* | (2006.01) |
| *A61L 27/54* | (2006.01) |

(52) U.S. Cl.
CPC .............. *A61L 27/16* (2013.01); *A61L 27/22* (2013.01); *A61L 27/227* (2013.01); *A61L 27/54* (2013.01); *C08F 220/34* (2013.01); *C08K 5/19* (2013.01); *C08L 25/06* (2013.01); *C08L 31/00* (2013.01); *C08L 33/08* (2013.01); *C08L 39/04* (2013.01); *A61L 2300/208* (2013.01); *A61L 2300/25* (2013.01); *A61L 2300/41* (2013.01); *A61L 2300/414* (2013.01); *C08L 2203/02* (2013.01)

(58) Field of Classification Search
None
See application file for complete search history.

(56) References Cited

U.S. PATENT DOCUMENTS

| | | | | |
|---|---|---|---|---|
| 2003/0064102 A1* | 4/2003 | Nakatsuka | ............... | A61K 6/20 424/486 |
| 2012/0148519 A1* | 6/2012 | Satake | ..................... | A61L 27/16 424/78.04 |
| 2016/0194424 A1* | 7/2016 | Higgs | .................... | G02B 1/041 522/182 |

\* cited by examiner

Primary Examiner — Brian Gulledge
(74) Attorney, Agent, or Firm — Gearhart Law LLC

(57) ABSTRACT

A cell growth inhibiting polymer for use in an ophthalmic implant includes at least one cell growth inhibiting monomer; and at least one other monomer selected from an acrylic monomer, a hydrophobic acrylic monomer, a hydrophilic acrylic monomer, a silicone monomer, a vinyl monomer and/or a collagen monomer.

9 Claims, 1 Drawing Sheet

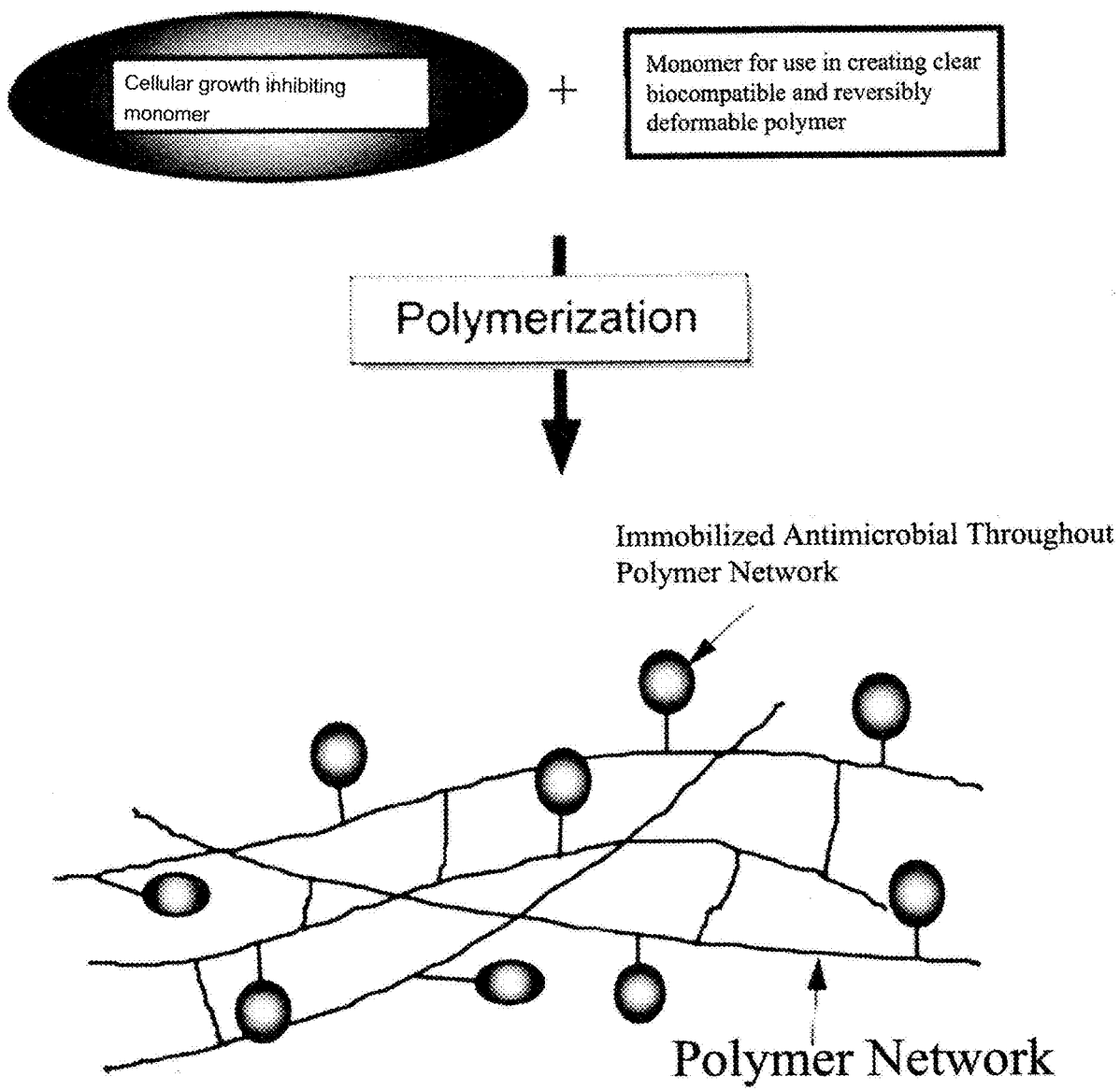

CELL GROWTH INHIBITING COPOLYMER FOR USE IN OPHTHALMIC IMPLANTS

CROSS-REFERENCE TO RELATED APPLICATIONS

This application claims the benefit of priority under 35 U.S.C § 119(e) to U.S. Provisional Patent Application Ser. No. 62/624,284, titled "CELL GROWTH INHIBITING COPOLYMER FOR USE IN OPHTHALMIC IMPLANTS," filed on Jan. 31, 2018, and to U.S. Provisional Patent Application Ser. No. 62/520,599, titled "CELL GROWTH INHIBITING COPOLYMER FOR USE IN OPHTHALMIC IMPLANTS," filed on Jun. 16, 2017, the disclosure of each of which is hereby incorporated by reference in their entireties for all purposes.

FIELD OF THE INVENTION

The present disclosure is directed to a cell growth inhibiting polymer obtained by copolymerizing at least one cell growth inhibiting monomer and at least one other monomer selected from acrylic, silicone, vinyl and/or collagen monomers. The copolymer of the present disclosure is cell growth inhibiting, clear, opaque, or translucent, biocompatible and reversibly deformable. Further, the copolymer according to the present disclosure can be used in ophthalmic implant devices.

BACKGROUND OF THE INVENTION

Cellular growth around ocular implants can decrease the clinical efficacy of the device. Examples of ocular implants include intraocular lenses (IOLs), glaucoma valves, corneal implants and artificial corneas, which are also known as keratoprostheses. Uncontrolled cellular growth after ophthalmic implant surgery often results in loss of vision.

In the case of IOLs, posterior chamber lenses are typically implanted within the natural capsular bag of the crystalline lens. Despite the best efforts of surgeons there are usually remaining lens epithelial cells on the posterior capsular membrane after the completion of cataract extraction and IOL implantation. These residual lens epithelial cells are capable of cell division and their growth across the visual axis can result in a condition known as posterior capsular opacification which can cause a decrease in the vision for the patient. Approximately one third of all cataract surgery patients will need to undergo a procedure known as YAG laser capsulotomy. This YAG laser procedure is generally regarded as being safe and effective, but can result in complications such as retinal tears, retinal detachment and loss of vision.

In the case of glaucoma valves, these devices are designed to create a permanent communication between the anterior chamber and the subconjunctival space thereby providing an alternative route for aqueous drainage. The intended effect of these devices is to reduce the intraocular pressure into a range that is healthy for the patient. However, it is well known in the art that the part of the glaucoma drainage device which lies within the subconjunctival space can often become enveloped by scar tissue, thereby obstructing the outflow of fluid and rendering the surgery ineffective.

For artificial corneas, a common situation which occurs in greater than 50% of artificial corneas that have a penetrating design, is the growth of a retroprosthetic membrane. These fibro-vascular membranes grow posterior to the implant and can obstruct the visual pathway. When this occurs, either laser or intraoperative excision may be required to restore vision. It is also possible in some cases for tissue to grow over the anterior part of the artificial cornea and obstruct vision in this way. Other inventors have recognized that cellular growth around an ophthalmic implant can decrease the efficacy of ophthalmic implant surgery. One alternative strategy that has been proposed is to either coat or covalently bond cell growth inhibiting chemicals to the surface of the implant. A limitation of this method is that coatings and covalently bonded chemicals may be eroded from the surface of the implant. Therefore, it is predictable that the cell growth inhibiting properties of these types of implants may decrease over time and worsen the results of surgery for the patient.

Another strategy, which has been proposed, is to infuse the polymer of the ophthalmic implant with a cell growth inhibiting metal ion. When a metal ion is infused into a polymer, the metal ion is free to move through the polymer and out of the polymer by diffusion. The metal ion is not covalently bonded to the polymer structure itself. The diffusion of the metal ion out of the polymer can be toxic. In particular, silver and copper metal have been proposed as agents to be infused into polymers for use in an ophthalmic implant. Although, the use of free metal ions has been used widely in commercial plastic goods and in some short-term disposable medical devices such as catheters, metal ions are known to be dangerous in the eye.

Argyrosis is the medical term for silver toxicity of the eye. Argyrosis has been reported to result in a slate gray discoloration of the conjunctiva and iris. Argyrosis has also been found to result in cataracts and retinal maculopathy, both of which are vision threatening conditions.

Copper toxicity in the eye results in a characteristic green ring around the cornea, which is termed a Kayser-Fleischer ring. Moreover, studies have demonstrated that copper toxicity can induce ocular complications such as intraocular inflammation (uveitis), hemorrhage, vitreous liquefaction, hypotony, iris ischemia and retinal damage.

There is only a finite amount of metal ion that is contained in an infused polymer. As the metal ion is depleted from the polymer by diffusion the cell growth inhibiting properties of the polymer will decrease and therefore the efficacy of the implanted device will also decrease.

For the stated reasons, there is a need for an improved new method of decreasing cellular growth after ophthalmic implant surgery which does not have the limitations of the prior art.

SUMMARY OF THE INVENTION

The disclosure provides a cell growth inhibiting polymer obtained by copolymerizing at least one cell growth inhibiting monomer and at least one monomer selected from an acrylic, silicone, vinyl and/or collagen monomer. The copolymer of the present disclosure is cell growth inhibiting, biocompatible and reversibly deformable. These characteristics are desirable for the optimal function of ophthalmic implants that are designed for implantation through small incisions. Moreover, because the entire co-polymer, not just the surface of the co-polymer, has cell growth inhibiting properties, ophthalmic implants made from this type of co-polymer will not lose their cell growth inhibiting properties even if the surface of the implant becomes eroded over time. This is particularly important for ophthalmic implants which are exposed to the surface of the eye, where blinking will cause erosion of the polymer material. When the surface of the polymer of the present disclosure is eroded, cell growth inhibiting polymer beneath the surface will still inhibit cellular growth and thereby continue to optimize the function of the implant.

BRIEF DESCRIPTION OF THE DRAWING

FIG. 1 illustrates an embodiment of the polymerization of a cell growth inhibiting, biocompatible, reversibly deformable polymer.

DETAILED DESCRIPTION OF THE EMBODIMENTS

The following description is presented to enable a person of ordinary skill in the art to make and use embodiments described herein. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the disclosure. The word "exemplary" is used herein to mean "serving as an example illustration." Any aspect or design described herein as "exemplary" is not necessarily to be construed as preferred or advantageous over other aspects or designs. Thus, the present disclosure is not intended to be limited to the examples described herein and shown but is to be accorded the scope consistent with the claims.

As used herein, reference to any biological drug includes any fragment, modification or variant of the biologic, including any pegylated form, glycosylated form, lipidated form, cyclized form or conjugated form of the biologic or such fragment, modification or variant or prodrug of any of the foregoing. As used herein, reference to any small molecule drug includes any salt, acid, base, hydrate, solvate, ester, isomer, or polymorph thereof or metabolite or prodrug of any of the foregoing. Abbreviations used herein have their conventional meaning within the chemical and biological arts.

It should be understood that the specific order or hierarchy of steps in the process disclosed herein is an example of exemplary approaches. Based upon design preferences, it is understood that the specific order or hierarchy of steps in the processes may be rearranged while remaining within the scope of the present disclosure. Any accompanying method claims present elements of the various steps in a sample order and are not meant to be limited to the specific order or hierarchy presented.

Accordingly, the present disclosure is directed to a cell growth inhibiting polymer obtained by copolymerizing at least one cell growth inhibiting monomer and at least one other monomer selected from an acrylic, silicone, vinyl and/or collagen monomers. The copolymer of the present disclosure is a cell growth inhibiting, biocompatible and reversibly deformable copolymer. Further, the copolymer according to the present disclosure can be used in ophthalmic implant devices. In other aspects, the disclosed copolymer material is a clear, opaque, or translucent material suitable for use in at least some applications.

In one embodiment, the cell growth inhibiting monomer is selected from quaternary ammonium-based monomers. An example of a quaternary ammonium-based monomer is methacryloyloxy dodecyl pyridium bromide (MDPB). MDPB has been used to reduce the risk of dental caries when copolymerized with dental adhesives and dental resins. MDPB has also been shown to inhibit mammalian cellular growth. Another example of a quaternary ammonium-based monomer is the monomer methacryloxyethyl cetyl ammonium chloride (DMAE-CB).

In another embodiment, it is also possible to increase the amount of cell growth inhibiting monomers that can be incorporated into polymeric materials and thereby enhance the cell growth inhibiting activity by modifying quaternary ammonium monomers to have two polymerizable methacrylic moieties.

In another embodiment, the cell growth inhibiting monomer may have primary, secondary or tertiary amino groups. Examples of these types of cell growth inhibiting monomers include but are not limited to phenylene ethynylene, dimethylamino methyl styrene, octylstyrene, dimethylamino ethyl acrylamide, aminoethyl acrylamide, n-butylacrylamide and diallylammonium salts that contain either secondary or tertiary amino groups.

In yet another embodiment, the cell growth inhibiting monomer is covalently linked to a cell growth inhibiting peptide. Examples of cell growth inhibiting peptides include: β-sheet peptides stabilized by two to four disulfide bridges (e.g., human α- and β-defensins, plectasin or protegrins), α-helical peptides (e.g., LL-37, cecropins or magainins), extended structures rich in glycine, proline, tryptophan, arginine or histidine (e.g., indolicidin), and loop peptides with one or disulfide bridge (e.g., bacteriocins).

In other embodiments, suitable acrylic monomers used to create a biocompatible, reversibly deformable polymer include at least one of the following monomers: glycerol monomethacrylate, 2-hydroxyethyl methacrylate, N-(2-hydroxypropyl)methacrylamide, hydroxypropyl methacrylate, poly(ethyleneglycol), monomethylether monomethacrylate, N-vinyl-2-pyrrolidone, isobutyl methacrylate, methyl methacrylate, N-octyl methacrylate, allyl phenyl ether, benzhydryl methacrylate, benzyl acrylate, N-benzyl methacrylamide, benzyl methacrylate, 2-(9H-carbazol-9-yl)ethyl methacrylate, 4-chlorophenyl acrylate, 1H,1H,7H-dodecafluoroheptyl methacrylate, 1H,1H,2H,2H-heptadecafluorodecyl acrylate, 1H,1H,2H,2H-heptadecafluorodecyl methacrylate, 1H,1H-heptafluorobutyl acrylate, 1H,1H,3H-hexafluorobutyl acrylate, 1H,1H,3H-hexafluorobutyl methacrylate, hexafluoroisopropyl methacrylate, 1H,1H,5H-octafluoropentyl acrylate, 1H,1H,5H-octafluoropentyl methacrylate, pentabromophenyl acrylate, pentabromophenyl methacrylate, pentafluorophenyl acrylate, pentafluorophenyl methacrylate, 1H,1H,3H-tetrafluoropropyl methacrylate, 2,4,6-tribromophenyl acrylate, 2,2,2-trifluoroethyl acrylate, 2,2,2-trifluoroethyl methacrylate, N-(3-aminopropyl)methacrylamide mono hydrochloride, 2-(N,N-dimethylamino) monoethyl methacrylate, methacrylic acid, 2-aminoethyl methacrylate hydrochloride, 4-(2-acryloxyethoxy)2-hydroxybenzophenone, phenyl acrylate, 4-methacryloxy-2-hydroxybenzophenone, 2-(2'-methacryloxy-5'-methylphenyl) benzotriazole, 2-cinnamoyloxyethyl acrylate, cinnamyl methacrylate, glycidyl cinnamate, 2-naphthyl methacrylate, ethylene glycol dimethacrylate, 1,4-phenylene diacrylate, and poly(ethylene glycol) diacrylate.

In an embodiment, the at least one other monomer is selected a hydrophobic acrylic monomer. Examples of hydrophobic acrylic monomers include but are not limited to:

Monomers of phenylethyl acrylate, phenylethyl methacrylate and butanediol diacrylate, which form a copolymer of phenylethyl acrylate and phenylethyl methacrylate, cross linked with butanediol diacrylate (AcrySof® IQ) available from Alcon, A Novartis Division, 6201 South Frees ray, Fort Worth, Tex. 76134-2001;

Monomers of ethyl acrylate, ethyl methacrylate, 2,2,2-trifluoroethyl methacrylate, cross linked with ethylene glycol dimethacrylate, which form a copolymer of ethyl acrylate, ethyl methacrylate, 2,2,2-trifluoroethyl methacrylate, cross linked with ethylene glycol dimethacrylate (Tecnis® (AMO)) available from Johnson & Johnson Vision Surgical, 1700 E St Andrew Pl, Santa Ana, Calif. 92705;

Monomers of phenylethyl methacrylate, n-butyl acrylate, and fluoroalkyl methacrylate, which form a cross linked copolymer of phenylethyl methacrylate, n-butyl acrylate, and fluoroalkyl methacrylate (AF-1® (HOYA)) available from Hoya Corporation, 7-5, Naka-Ochiai 2-chome, Shinjuku-ku Tokyo, Japan;

Monomers of phenylethyl acrylate, phenylethyl methacrylate, and butanediol diacrylate, which form a copolymer of phenylethyl acrylate and phenylethyl methacrylate, cross-linked with butanediol diacrylate (HI56) available from Contamac® Ltd., Carlton House, Shire Hill, Saffron Walden, Essex CB11 3AU;

Monomers of 2-phenylethyl acrylate and 2-phenylethyl methacrylate, which form a copolymer of 2-phenylethyl acrylate and 2-phenylethyl methacrylate (BENZ HF-1.2) available from Benz Research & Development Corporation, 6447 Parkland Drive, Sarasota, Fla. 34243; and Monomers of 2-phenylethyl acrylate and 2-phenylethyl methacrylate, which form a copolymer of 2-phenylethyl acrylate and 2-phenylethyl methacrylate (Benz HF-2) available from Benz Research & Development Corporation, 6447 Parkland Drive, Sarasota, Fla. 34243.

In an embodiment, the at least one other monomer is selected a hydrophilic acrylic monomer. Examples of hydrophilic acrylic monomers include but are not limited to:

Monomers of hydroxyethyl methacrylate and methyl methacrylate, which form a copolymer of hydroxyethyl methacrylate and methyl methacrylate (CI26) available from Contamac® Ltd., Carlton House, Shire Hill, Saffron Walden, Essex CB11 3AU;

Monomers of hydroxyethyl methacrylate and methyl methacrylate, which form a copolymer of hydroxyethyl methacrylate and methyl methacrylate (MICS22) available from Contamac® Ltd., Carlton House, Shire Hill, Saffron Walden, Essex CB11 3AU;

Monomers of hydroxyethyl methacrylate and methyl methacrylate, which form a copolymer of hydroxyethyl methacrylate and methyl methacrylate (CI18) available from Contamac® Ltd., Carlton House, Shire Hill, Saffron Walden, Essex CB11 3AU;

Monomers of 2-hydroxyethyl methacrylate and 2-ethoxyethyl methacrylate, which form a copolymer of 2-hydroxyethyl methacrylate and 2-ethoxyethyl methacrylate (Benz IOL 125 available from Benz Research & Development Corporation, 6447 Parkland Drive, Sarasota, Fla. 34243; and Monomers of 2-hydroxyethyl methacrylate and methyl methacrylate, which form a copolymer of 2-hydroxyethyl methacrylate and methyl methacrylate (BenzFlex 26) available from Benz Research & Development Corporation, 6447 Parkland Drive, Sarasota, Fla. 34243.

In other embodiments, the silicone monomers used to create a biocompatible, reversibly deformable polymer include at least one of the following monomers: dimethylsiloxane and/or dimethyldiphenylsiloxane monomers.

In other embodiments, the vinyl monomers used to create a biocompatible, reversibly deformable polymer include at least one of the following monomers: N-vinyl-2-pyrrolidone and/or N-vinyl carbazole monomers.

In other embodiments, the collagen monomers used to create a clear, opaque, or translucent, biocompatible, reversibly deformable polymer include at least one of the following monomers: naturally derived type I-XXVIII collagen monomers, recombinant collagen monomers and fragments thereof, and/or synthetic collagen monomers and fragments thereof.

FIG. 1 illustrates an embodiment of the polymerization of a cellular growth inhibiting, reversibly deformable polymer. In this FIGURE, the cellular growth inhibiting polymers are obtained by copolymerizing at least one cellular growth inhibiting monomer with at least one monomer selected from an acrylic, silicone, vinyl and/or collagen monomer. After polymerization, the resulting polymeric network includes the immobilized cellular growth inhibiting polymer spaced throughout the network.

While the inventive features have been particularly shown and described with reference to preferred embodiments thereof, it will be understood by those in the art that the foregoing and other changes may be made therein without departing from the sprit and the scope of the disclosure. Likewise, the various diagrams may depict an example architectural or other configuration for the disclosure, which is done to aid in understanding the features and functionality that can be included in the disclosure. The disclosure is not restricted to the illustrated example architectures or configurations but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied alone or in some combination, to one or more of the other embodiments of the disclosure, whether or not such embodiments are described, and whether or not such features are presented as being a part of a described embodiment. Thus, the breadth and scope of the present disclosure should not be limited by any of the above-described exemplary embodiments.

What is claimed is:

1. A cell growth inhibiting polymer for use in an ophthalmic implant, comprising: at least one cell growth inhibiting monomer; and at least one other monomer selected from monomers of phenylethyl acrylate, phenylethyl methacrylate and butanediol diacrylate, which forms a copolymer of phenylethyl acrylate and phenylethyl methacrylate, cross linked with butanediol diacrylate;
   wherein the at least one cell growth inhibiting monomer is a quaternary ammonium-based salt monomer;
   and wherein the quaternary ammonium-based salt monomer is selected from methacryloyloxydodecylpyridium bromide (MDPB), methacryloxyethyl cetyl ammonium chloride (DMAE-CB), 2-methacryloxyethyl dodecyl methyl ammonium bromide (MAE-DB), 2-methacryloxyethyl hexadecyl methyl ammonium bromide (MAE-HB), and/or bis(2-methacryloxyethyl) dimethyl ammonium bromide (IDMA-1).

2. The cell growth inhibiting polymer according to claim 1, wherein the cell growth inhibiting polymer is clear, opaque, or translucent.

3. The cell growth inhibiting polymer according to claim 1, wherein the cell growth inhibiting polymer is reversibly deformable.

4. The cell growth inhibiting polymer according to claim 1, wherein the ophthalmic implant is an artificial cornea or a glaucoma valve.

5. An article of manufacture, comprising:
an ophthalmic implant, the implant comprising a cell growth inhibiting polymer, the cell growth inhibiting polymer comprising: at least one cell growth inhibiting monomer; and at least one other monomer selected from monomers of phenylethyl acrylate, phenylethyl methacrylate and butanediol diacrylate, which forms a copolymer of phenylethyl acrylate and phenylethyl methacrylate, cross linked with butanediol diacrylate;
wherein the at least one cell growth inhibiting monomer is a quaternary ammonium-based salt monomer;
and wherein the quaternary ammonium-based salt monomer is selected from methacryloyloxydodecylpyridium bromide (MDPB), methacryloxyethyl cetyl ammonium chloride (DMAE-CB), 2-methacryloxyethyl dodecyl methyl ammonium bromide (MAE-DB), 2-methacryloxyethyl hexadecyl methyl ammonium bromide (MAE-HB), and/or bis(2-methacryloxyethyl) dimethyl ammonium bromide (IDMA-1).

6. The article of manufacture according to claim 5, wherein the cell growth inhibiting polymer is clear, opaque, or translucent.

7. The article of manufacture according to claim 5, wherein the cell growth inhibiting polymer is reversibly deformable.

8. The article of manufacture according to claim 5, wherein the ophthalmic implant is an artificial cornea.

9. The article of manufacture according to claim 5, wherein the ophthalmic implant is a glaucoma valve.

* * * * *